United States Patent [19]

Rausch et al.

[11] Patent Number: 4,677,196

[45] Date of Patent: Jun. 30, 1987

[54] PURIFICATION AND ACTIVATION OF PROTEINS FROM INSOLUBLE INCLUSION BODIES

[75] Inventors: Steven K. Rausch, Terre Haute, Ind.; Hsi Meng, Northbrook, Ill.

[73] Assignee: International Minerals & Chemical Corp., Terre Haute, Ind.

[21] Appl. No.: 773,174

[22] Filed: Sep. 6, 1985

[51] Int. Cl.$^4$ .......................... C07K 3/20; C12P 21/00
[52] U.S. Cl. ...................................... 530/412; 530/416; 530/417; 530/422; 530/820; 435/68; 435/70
[58] Field of Search ................. 260/112 R; 435/68, 70

[56] References Cited

U.S. PATENT DOCUMENTS

| 4,426,323 | 1/1984 | Jain | 435/68 |
| 4,511,502 | 4/1985 | Builder | 260/112 R |
| 4,511,503 | 4/1985 | Alson | 260/112 R |
| 4,518,526 | 5/1985 | Olson et al. | 260/112 R |

OTHER PUBLICATIONS

Kapp et al., *Anal. Biochem.* 91, 1978, pp. 230–233.

*Primary Examiner*—John Kight
*Assistant Examiner*—Garnette D. Draper
*Attorney, Agent, or Firm*—George R. Repper; Thomas L. Farquer; Wendell R. Guffey

[57] ABSTRACT

Purification and activation of proteins produced in transformant microorganisms as insoluble, biologically inactive inclusion bodies can be effected by solubilizing the inclusion bodies in SDS; dialyzing or refrigerating the protein solution to remove a portion of the SDS; chromatographing the protein solution on an ion-retardation resin to remove the remaining SDS from the protein; and chromatographing the protein solution thus obtained on an anion-exchange resin.

20 Claims, No Drawings

PURIFICATION AND ACTIVATION OF PROTEINS FROM INSOLUBLE INCLUSION BODIES

BACKGROUND OF THE INVENTION

This invention relates to methods for purifying and activating proteins that are produced as insoluble, biologically inactive inclusion bodies in microorganisms that have been transformed with recombinant DNA expression vectors to direct expression of the protein of interest.

Recombinant DNA technology allows the insertion of a vector carrying foreign (heterologous) DNA into a microorganism in a manner which allows the heterologous DNA to be expressed; that is, the vector contains genetic instructions which direct the microorganism to produce a protein which is encoded by a portion of the heterologous DNA sequence. By growing transformant microorganisms in a fermentor and subjecting them to conditions under which the heterologous DNA is expressed, valuable proteins can be produced in large quantity at relatively low cost.

Unfortunately, many heterologous proteins which are produced in transformant microorganisms do not fold into their native three-dimensional conformation within the host cell environment. This improper folding of the expressed protein has several untoward consequences. In the first place, the improperly folded proteins tend to form aggregates which are insoluble within the host cell. These insoluble aggregates are recognizable within the cell as "inclusion bodies", sometimes also referred to as "refractile bodies" and/or "protein granules". The formation of inclusion bodies may also be partially caused by oligomerization of the protein, that is, the formation of covalent intermolecular disulfide bonds. Not only are the improperly folded proteins insoluble, but also they are biologically inactive. As exemplary of heterologous proteins which form insoluble, biologically inactive inclusion bodies upon expression in a host cell, one can mention animal growth hormones and growth factors such as bovine growth hormone, porcine growth hormone and somatomedin.

In order to produce useful proteins, it is necessary to convert the improperly folded inclusion body proteins into their native conformations, in which they are soluble and biologically active. Moreover, it is necessary to purify the protein in order to remove contaminating cell debris and other proteins produced by the host cell. A number of schemes have been proposed for converting inclusion body proteins into their soluble, native configurations. Unfortunately, these schemes are often incompatible with protein purification procedures, such as ion-exchange chromatography. The conditions of purification tend to inhibit the ability to maintain the protein in solution, often resulting in a substantial loss of protein due to reaggregation and precipitation. Most of the schemes proposed for recovering proteins from inclusion bodies in purified, soluble, biologically active form have resulted in very low yields of the proteins produced by the microorganisms.

U.S Pat. No. 4,511,503 discloses a typical scheme for recovering proteins from inclusion bodies in transformant microorganisms. The inclusion body proteins are treated with a strong denaturant, which causes the improperly folded protein molecules to unfold and become soluble. The denaturant is subsequently removed, for example, by dialysis, in order to allow the protein to refold into its native conformation. The most commonly employed strong denaturant in schemes of this type has been guanidine hydrochloride.

U.S. Pat. No. 4,511,502 discloses a similar process wherein the solubilized protein/denaturant solution is passed over a molecular sieve or centrifuged at high speed to remove higher molecular weight components.

U.S. Pat. No. 4,518,526 also discloses a similar process. In this process, the transformant cell culture is treated with a buffered solution of sufficient ionic strength to solubilize most of the host cell protein, whereas the heterologous protein remains insoluble. The cells are then lysed, the supernatant containing the solubilized host cell protein removed and the insoluble inclusion bodies solubilized in the strong denaturant.

Other publications disclosing denaturation/renaturation schemes for converting inclusion body proteins into their soluble, native conformations include PCT publication No. WO 83/04418, European Patent Application Publication No. 0 123 928, European Patent Application Publication No. 0 121 775, European Patent Application Publication No. 0 116 778 and European Patent Application Publication No. 0 114 507.

As previously indicated, most of the proposed denaturation/renaturation schemes have employed guanidine hydrochloride as the denaturant. While guanidine hydrochloride is characterized by an excellent ability to solubilize inclusion body proteins, its use entails some problems. Upon dialysis against denaturant-free buffer to remove the guanidine hydrochloride, a substantial amount of the solubilized protein reaggregates, apparently due to improper refolding. Moreover, when guanidine-solubilized protein is purified by methods such as ion-exchange chromatography—which are necessary to obtain the degree of purity required in the final product—substantial losses of protein are incurred due to reaggregation. Fouling and plugging of the column tends to occur in an inordinately short time, severely limiting the useful life of the column. Typically, we have found that guanidine solubilization of bovine growth hormone inclusion bodies, followed by ion-exchange chromatography, yielded only 4–12% product recovery.

Another major problem associated with the use of guanidine hydrochloride—one which is particularly important from a commercial production standpoint—is its high cost. It would be highly desirable to employ a solubilizing agent which is comparable to guanidine hydrochloride in its ability to solubilize inclusion body proteins, but without the associated high cost of guanidine. U.S. Pat. No. 4,511,503 suggests the use of detergents such as sodium dodecyl sulfate (SDS) as denaturants. However, there is no demonstration of its use, nor is there proposed a method for removing the detergent from the protein and purifying the protein.

Detergents such as SDS are highly effective denaturing agents. Moreover, SDS is a much less expensive reagent than guanidine hydrochloride. Accordingly, its potential use in recovering inclusion body proteins is attractive from the standpoint of commercial production economics. Compared with guanidine hydrochloride, however, SDS binds to the denatured protein much more tightly, making its complete removal from the protein problematical.

O. H. Kapp and S. W. Vinogradov demonstrated that SDS could be removed from several proteins by chromatography on the ion-retardation resin AG11A8

(*Anal. Biochem.*, 91:230–233 [1978]). It was said that from 0.1 to 1.4 moles of SDS remained on each mole of protein treated in this manner. K. Weber and D. J. Kuter demonstrated that SDS could be removed from aspartate transcarbamylase by incubation in urea and subsequent anion-exchange chromatography (*J. Biol. Chem.*, 246;450–4509 [1971]). In both instances, however, the starting proteins were in pure, biologically active form. There is no suggestion of a method for efficiently recovering protein in a pure, biologically active form from insoluble, intracellular inclusion bodies.

SUMMARY OF THE INVENTION

This invention provides an efficient, economical method for recovering proteins that are produced as insoluble, biologically inactive inclusion body proteins in transformant microorganisms. The method of the invention provides for conversion of the protein into its soluble, native conformation and concomitant purification of the protein. In the method of the invention, a detergent such as SDS is used as a denaturant, rather than a more expensive denaturant such as guanidine hydrochloride. Quite surprisingly, we have found that losses of protein using the method of the invention to purify and activate the protein are substantially less than with the guanidine hydrochloride method. Using SDS as the denaturant in accordance with the method of the invention, we have obtained recovery yields of up to about 30%, based on the amount of protein present in the inclusion bodies. These yields are significantly higher than those obtainable with prior processes using guanidine hydrochloride as the denaturant. The protein product obtained by the method of the invention is soluble, essentially homogeneous and essentially free of SDS.

More particularly, the invention provides a method for purifying and activating a protein that is produced as an insoluble, biologically inactive inclusion body in a transformant microorganism which comprises:

(a) extracting the inclusion bodies into a buffered solution of sodium dodecyl sulfate to solubilize the protein;

(b) chromatographing the protein solution on an ion-retardation resin to remove the remainder of the sodium dodecyl sulfate from the protein; and (c) chromatographing the protein solution from step (b) on an anion-exchange resin.

In a preferred embodiment of the invention, the protein-containing sodium dodecyl sulfate solution is treated to remove a substantial amount of the sodium dodecyl sulfate prior to chromatography on the ion-retardation resin. Removal of a portion of the sodium dodecyl sulfate can be accomplished by dialysis against a buffer solution or by refrigeration of the solution.

DETAILED DESCRIPTION OF THE INVENTION

The method of the invention is used to purify and activate proteins which are produced in the form of insoluble, biologically inactive inclusion bodies in transformant microorganisms, i.e., microorganisms which have been transformed with recombinant DNA vectors that direct the expression of genes coding for heterologous proteins. Generally, the proteins which can be purified and activated by the method of the invention are negatively charged proteins which are basic under the processing conditions that are described below in detail. In specific embodiments of the invention, the proteins which are purified and activated are animal growth hormones such as bovine growth hormone (bGH) or porcine growth hormone (pGH).

It is to be understood that reference herein to proteins generally—e.g., hormones and enzymes—or to specific proteins such as bGH and pGH is not intended to be restricted to molecules which contain the full amino acid sequence of the natural protein. Rather, it is also intended to include fragments of the protein having various portions of the sequence deleted and proteins or fragments thereof having various substitutions or modifications in their natural sequences (i.e., analogues) which do not destroy the biological activity of the molecules.

The genes for bGH and pGH have been cloned onto expression vectors and used to transform *E. coli* host cells. European Patent Application Publication No. 0 103 395 describes the construction of a transformant strain of *E. coli* containing a first plasmid which codes for $\Delta 9$(Ser)bGH (bGH less its 9 N-terminal amino acids and having an additional serine residue at the N-terminus) under the control of the $\lambda P_L$ promoter-operator and which has a Shine-Dalgarno region derived from bacteriophage mu. The transformant also contains a second plasmid, pcI857, which codes for the production of the cI857 temperature-sensitive repressor protein. The repressor protein can be inactivated by raising the temperature to about 42° C., thereby inducing expression of $\Delta 9$(Ser)bGH. A transformant strain of this type, *E. coli* HB101 ($P_L$-mu-$\Delta 9$(Ser)bGH and pcI857) has been deposited, with the designation *E. coli*, IMC No. 1, at The American Type Culture Collection, Rockville, Md., with accession No. 53030.

Construction of a similar transformant strain which codes for the production of $\Delta 7$pGH (porcine growth hormone less its first 7 N-terminal amino acids) is described in European Patent Application Publication No. 0 104 920. A transformant strain of this type, *E. coli* HB101 ($P_L$-mu-$\Delta 7$pGH and pcI857) has been deposited, with the designation *E. coli*, IMC No. 2, at The American Type Culture Collection, Rockville, Md., with accession No. 53031.

*E. coli*, IMC No. 1 and *E. coli*, IMC No. 2 are prolific producers of $\Delta 9$(Ser)bGH and $\Delta 7$pGH, respectively. In both instances, the expressed protein is sequestered within the cell in the form of insoluble, biologically inactive inclusion bodies which are visible under a microscope.

After the transformant cells have been grown in a fermentor and the protein of interest has been expressed and allowed to accumulate within the cells as inclusion bodies, the transformant cells are generally lysed, either mechanically, chemically or enzymatically, to allow isolation of the inclusion bodies which are sequestered within the cells. Prior to employing the method of the invention, the inclusion bodies can be separated from the bulk of the remainder of cellular material by centrifugation and washing in a buffer to produce a wet inclusion body paste.

The inclusion bodies are extracted into a buffered solution of SDS to solubilize the protein. The amount of SDS in the buffered solution is an amount sufficient to dissolve the protein. Preferably, the buffered solution contains from about 0.1% to 5.0% SDS, most preferably about 1%. We have found that high pH buffers, i.e., from about pH 8.5 to pH 11 are best suited to maintaining the protein in a solubilized form. A suitable buffer solution is 0.02 M to 0.1 M ethanolamine-HCl, carbonate-bicarbonate or borate buffer. If desired, a reducing agent, such as 2-mercaptoethanol, may also be present in the SDS solution in an amount sufficient to prevent the formation of intermolecular disulfide bonds during the recovery process. We have not found, however, that the use of reducing agents results in a significant increase in the yield of soluble, biologically active protein. Disaggregation of the inclusion bodies in the SDS solution generally occurs over a period of about 4 to 18 hours.

Once the inclusion body proteins have been solubilized in the SDS solution and allowed to become disaggregated, it is preferred to remove a substantial amount of the SDS from the solution prior to chromatography on the ion-retardation resin. Removal of a substantial amount of the SDS can be effected by dialysis against a non-SDS-containing buffer solution or by reducing the temperature of the SDS-containing solution. Although it is possible to load the SDS-containing solution directly onto the ion-retardation resin without a preliminary SDS removal step, it is impractical to do so, since removal of all the SDS by means of the ion-retardation resin alone would require an impractically large ion-retardation resin column or would entail unacceptably low throughput from a commercial production standpoint. The amount of SDS removed in the preliminary step prior to ion-retardation chromatography can vary, depending primarily on protein concentration. Typically, from about 40% to about 70% of the SDS initially present in the solution is removed.

As used herein, the term "dialysis" refers to any technique in which SDS is removed from the protein solution by selective transport of SDS ions across a semi-permeable membrane with retention of the desired protein molecules on the other side of the membrane. Any of the known methods of dialysis may be used with a variety of types of equipment. For example, SDS may be dialyzed from the solution using hollow fiber ultrafiltration systems. In these systems, a SDS-free buffer solution of low ionic strength is circulated around bundles of semi-permeable hollow fibers. Examples of low ionic strength buffer solutions for use in dialysis include 0.02 to 0.1 M ethanolamine buffer, carbonate-bicarbonate buffer ($HCO_3^-/CO_3^{--}$) or sodium borate buffer. Buffer solutions below about 0.02 M can result in solubility problems, whereas buffers in excess of about 0.1 M (although useful) are unnecessary. Small molecules in the protein solution that flows through the fibers are capable of passing through the membranous fiber wall so as to reduce the ionic strength of the protein solution. Other known dialysis techniques including, but not limited to, diafiltration and sack dialysis can also be employed to remove SDS from the protein solution.

As noted above, refrigeration of the SDS-containing protein solution can be used to remove a portion of the SDS from the protein. The solution containing the solubilized inclusion body protein generally is a low ionic strength buffer solution, such as 0.02 to 0.1 M carbonate-bicarbonate buffer or borate buffer. A portion of the SDS can be removed from the protein by cooling the buffer solution to a temperature between the freezing point of the solution and about 2° C. for a period of about 4 hours, whereupon SDS precipitates out of solution and can be removed by filtration or centrifugation.

The dialysis or refrigeration step removes a substantial amount of the SDS from the protein solution. However, some of the SDS will remain tightly bound to the protein. In order to complete the removal of SDS from the protein, the protein solution is chromatographed on an ion-retardation resin. An ion-retardation resin is a resin which contains both anion and cation exchange sites and is capable of selectively retarding the flow of ionic substances. It is, therefore, capable of separating the weakly ionic protein molecules from the SDS ions, which pass through the resin more slowly. A preferred ion-retardation resin for use in the method of the invention is the resin known as AG11A8, which is commercially available from Bio-Rad Laboratories, Richmond, Calif. It is produced by polymerizing acrylic acid inside the resin AG1X8 (a styrene-divinylbenzene copolymer with attached quaternary ammonium groups) and thus contains strongly basic charged cations, $\phi CH_2N^+(CH_3)_3$, and weakly acidic anions, $RCH_2COO^-$.

The ion-retardation resin is generally employed in the form of a packed column. The column is equilibrated by passing buffer solution (absent protein) through the column until pH and conductivity of feed and eluent match. The protein solution containing SDS is then loaded onto the column. While a variety of eluents can be used to elute the protein from the column, it is preferred to elute the column using a buffered solution of 0.02 to 0.1 M ethanolamine, preferably about 0.05 M ethanolamine. The protein, which passes through the column more rapidly than the SDS, is collected in the early-stage eluate. An AG11A8 column can be regenerated by washing with multiple volumes of 1.0 M $NH_4Cl$, followed by multiple volumes of deionized water or simply by washing with large volumes of water.

The eluate from the ion-retardation resin contains SDS-free protein which has been refolded into its native configuration. The eluate from the ion-retardation resin is loaded onto an anion-exchange resin, which is generally in the form of a packed column. One can mention, as merely illustrative of suitable anion-exchange resins, DE-52, DE-53, DEAE-Sepharose CL-6B, Cellufine AM, QAE-Sephadex, Q-Sepharose, QAE-Cellulose and DEAE-Trisacryl. The anion-exchange resin preferably contains a high degree of substitution with cationic groups, such as quarternary ammonium ions, attached to a polysaccharide support, such as dextran, agarose or cellulose, or attached to a polyacrylate support. Exemplary of such preferred resins is DE-53. Recently developed synthetic resins which are known to be useful in protein purification columns, such as Trisacryl (commercially available from LKB Instruments), can be employed. The protein in the anion-exchange column eluate can be concentrated, if desired, using known techniques such as ultrafiltration.

The purified protein can be eluted from the anion-exchange column using buffered saline solution preferably at pH 8.5 or above, with a salt concentration of 0 to 0.1 molar.

After each step in the method of the invention, i.e., after extraction into SDS, dialysis or refrigeration, chromatography on the ion-retardation resin and anion-exchange chromatography, the protein-containing solution can be centrifuged, if found desirable or necessary, in order to remove any precipitates which may have formed. The precipitates can either be discarded or recycled.

The following examples are intended to further illustrate the practice of the invention and are not intended to limit the scope of the invention in any way.

EXAMPLE I

Purification and Activation of Δ7 Porcine Growth Hormone

Inclusion bodies were obtained from *E. coli*, IMC No. 2 (ATCC 53031), which had been cultured under Δ7pGH-producing conditions. The cells from the fermentor were harvested by centrifugation from the fermentor beer, suspended in 0.1 M phosphate buffer, pH 7.8, 10 mM EDTA, and lysed by multiple passage through a Manton-Gaulin homogenizer. The crude inclusion bodies were harvested by centrifugation and washed twice in this same buffer.

Twenty-four grams of these inclusion bodies were extracted in 1000 ml of 0.1 M ethanolamine-HCl, pH 9.0, 1% SDS, by stirring overnight at room temperature. The resulting extract was dialyzed twice against 16 liters of 20 mM ethanolamine-HCl, pH 9.0, over a period of 48 hours. Residual insoluble material was removed by centrifugation at 15,000× g for 30 minutes. The clarified extract was chromatographed on a 10×30 cm column of AG11A8 ion-retardation resin equilibrated in 50 mM ethanolamine-HCl, pH 9.8. The column was developed in this same buffer at a linear flow rate of 0.3 cm/min. The fractions-containing protein were then chromatographed on a 4.4×25 cm column of DE-53 cellulose equilibrated in 50 mM ethanolamine-HCl, pH 9.0. After loading the extract, the column was washed with two column volumes of this buffer to elute contaminants in the void volume. NaCl was then added to the buffer to a final concentration of 0.1 M, which caused the elution of the Δ7pGH.

The fractions containing pure Δ7pGH were concentrated tenfold over an ultrafiltration membrane (10,000 dalton cut-off) under nitrogen pressure, exhaustively dialyzed against 0.25 mM sodium bicarbonate, 0.21 mM sodium carbonate, pH 9.7, concentrated an additional threefold, and lyophilized. The final product (992 mg) was essentially pure Δ7pGH. Overall yield, based on the original fermentor titer, was 20.2%.

EXAMPLE II

Purification and Activation of Δ7 Porcine Growth Hormone

Inclusion bodies were obtained from *E. coli*, IMC No. 2 (ATCC 53031), which had been cultured under Δ7pGH-producing conditions. The cells were centrifuged out of the fermentor beer and resuspended in 0.1 M Tris-HCl, pH 7.8, 10 mM EDTA, 5% sucrose. Lysozyme was added to 200 mg/liter and incubated at 28° C. for 40 minutes, at which time the cells were again centrifuged out. They were resuspended in 0.1 M phosphate buffer, pH 7.8, containing 10 mM EDTA and 0.5 mM reduced glutathione, and lysed by passing twice through a Manton-Gaulin homogenizer at 6000–8000 psi. Phenylmethylsulfonyl fluoride was added to 0.5 mM in order to inhibit protease activity and the crude inclusion bodies were centrifuged out. The pellet was washed three times by resuspension in 0.1 M Tris-HCl, pH 7.8, 2 M urea, 1% Triton X-100, 0.5 mM dithioerythritol (DTE) followed by centrifugation. The remaining pellet was washed twice more with 0.1 M Tris-HCl, pH 7.8, 0.5 mM DTE.

One-half gram of this pellet was extracted in 100 volumes (50 ml) of "Cornell buffer minus NaCl" ("CB": 25 mM sodium bicarbonate, 21 mM sodium carbonate, pH 9.8), 1% w/v SDS, 10 mM DTE, 1 mM EDTA, by stirring for 4 hours under a nitrogen blanket. This extract was then diluted to 400 ml with CB/10 mM DTE/1 mM EDTA and dialyzed against 10 volumes of CB/5 mM 2-mercaptoethanol (BME)/1 mM EDTA. The dialyzed extract was chromatographed at a flow rate of 100 ml/hr over a 2.5×35 cm column of AG11A8 ion-retardation resin equilibrated in CB/5 mM BME/1 mM EDTA. The protein-containing eluate was then chromatographed at 180 ml/hr flow rate on a 4.4×15 cm column of DEAE-Trisacryl equilibrated in this same buffer. A single peak was seen to elute in the void volume of the column and contained greater than 95% pure Δ7pGH. The relevant fractions were pooled, concentrated threefold over an ultrafiltration membrane (5000 dalton cut-off), dialyzed extensively against 1% CB (0.25 mM sodium bicarbonate, 0.21 mM sodium carbonate) and lyophilized. The final product (26.5 mg protein) represented a recovery of 14.5% based on the total amount of protein in the original extract.

EXAMPLE III

Purification and Activation of Δ7 Porcine Growth Hormone

Inclusion bodies were obtained from *E. coli*, IMC No. 2 (ATCC 53031), which had been cultured under Δ7pGH-producing conditions, in the same manner as was outlined in Example I. One gram of these inclusion bodies were extracted in 100 volumes (100 ml) of CB/1% SDS/20 mM BME/1 mM EDTA by stirring for 3 hours under a nitrogen blanket. The extract was dialyzed against 2×40 volumes of CB/1 mM EDTA and diluted to 400 ml with CB/5 mM BME/1 mM EDTA. It was then chromatographed on a 4.4×30 cm column of AG11A8 resin at 250 ml/hr in CB/5 mM BME/1 mM EDTA. Those fractions containing protein were pooled and chromatographed over a 4.4×30 cm column of DEAE-Trisacryl at 150 ml/hr in this same buffer. When no protein eluted in the void fractions, NaCl was added to a final concentration of 0.2 M, causing a single peak, containing highly purified Δ7pGH, to elute. The fractions containing pGH were pooled, exhaustively dialyzed against 1% CB, concentrated 15-fold over an ultrafiltration membrane under 65 psi (5000 dalton cut-off), and lyophilized. The resulting product contained 27 mg of Δ7pGH which was greater than 95% pure by gel electrophoretic analysis. The overall yield, based upon total protein content of the original extract, was 21%.

EXAMPLE IV

Purification and Activation of Δ7 Porcine Growth Hormone

The inclusion bodies used were prepared from *E. coli*, IMC No. 2 (ATCC 53031), which had been cultured under Δ7pGH-producing conditions, in the same manner as was outlined in Example I. Three grams of these inclusions were extracted into 100 volumes of CB/1.8% SDS/20 mM DTE/1 mM EDTA by stirring for 3.5 hours. This extract was then dialyzed against 2×16 volumes of CB/5 mM BME/1 mM EDTA and chromatographed on a 4.4×24 cm AG11A8 column equilibrated in the same buffer. The column was developed with this buffer at a linear flow rate of 0.3 cm/min. The fractions containing protein were pooled and extensively dialyzed against 50 mM ethanolamine-HCl, pH 9.0, and chromatographed on a 4.4×20 cm column of DE-53 in the same buffer. No protein eluted in the breakthrough fractions, but addition of 0.1 M NaCl to the buffer caused elution of the Δ7pGH. The relevant fractions were pooled, diafiltered in a stirred cell over a 5000-dalton cut-off membrane against 5 mM Tris-HCl, pH 7.4, concentrated roughly tenfold, and lyophilized. The final product was 29 mg of powder that was greater than 90° pure Δ7pGH by gel analysis. Overall yield, based on the original Δ7pGH content of the inclusion bodies, was 5.8%.

EXAMPLE V

Purification and Activation of Δ9(Ser)bGH

Inclusion bodies were obtained from *E. coli*, IMC No. 1 (ATCC 53030), which had been cultured under Δ9(Ser)bGH-producing conditions. Live cells harvested from the fermentor beer (830.6 g cell paste) were temporarily stored at −85° C., then thawed, treated with lysozyme, homogenized, centrifuged and resuspended in 0.1 M phosphate buffer, pH 7.8, 10 mM EDTA. The cells were then lysed by three passages through a Manton-Gaulin homogenizer at 6000 psi. Following centrifugation (14,000× g, 20 min.), 357.5 g of inclusions were recovered. These were resuspended in 500 ml 100 mM Tris-HCl, pH 7.5, 0.5 mM dithiothreitol, 0.5 mM PMSF and stored at −85° C. About one-third of this material (131.5 g) was thawed and used in the purification/activation process. The crude inclusions were washed once with 10 volumes of 0.2 M $NaH_2PO_4$, 10 mM EDTA, pH 7.8, and centrifuged to yield 109.3 g of pellet. The washed inclusions were solubilized by 60 sec. homogenization into 6,560 ml of 0.1 M ethanolamine-HCl, pH 9.0, 1% SDS. After overnight stirring, this extract was diafiltered against ten volumes of 20 mM ethanolamine-HCl, pH 9.0, which lowered the SDS level to 4.8 mg/ml. The extract was centrifuged at 8000 rpm for 30 minutes to remove particulates, diluted 1:1 in 20 mM ethanolamine-HCl, pH 9.0, and chromatographed on a 15-liter AG11A8 column. The Δ(Ser)bGH pool from the AG11A8 column was then chromatographed on a 1.85-liter DE-52 column equilibrated in 50 mM ethanolamine-HCl, pH 9.0 at 16 ml/min. There was a considerable amount of protein in the breakthrough fraction as indicated by the $A_{280}$. This plus a one column-volume wash with 50 mM ethanolamine-HCl, pH 9.0, constituted 18 liters of material. Since eluate was still exhibiting non-zero $A_{280}$, an additional 8 liters of material was collected. Approximately 2 column-volume washes each of 0.1 and 1.0 M NaCl followed; those were collected separately. The breakthrough fractions contained greater than 95% pure Δ9(Ser)bGH by SDS-PAGE analysis. Protein determination by Coomassie Blue dye binding assay showed approximately 3.2 g of protein in the pooled eluate. The NaCl washes also contained Δ9(Ser)bGH, but it was almost completely covalently aggregated. The 18 liters of DE-52 eluant from the DE-52 column were concentrated 4.5-fold in an Amicon DC2 ultrafiltration unit, after which air injected during recirculation caused frothing and precipitation.

The precipitate was removed by filtration through Whatman No. 2 filter paper and final concentration to about 2 liters was accomplished over a YM-10 membrane. The protein solution was then dialyzed (sack dialysis) three times against 36 liters of 1% Cornell buffer minus NaCl and lyophilized to yield 2.8 grams of product.

The 8 liters of additional material washed off the DE-52 column was analyzed and appeared to constitute essentially pure Δ9(Ser)bGH. After concentration to 1.3 liters in a stirred cell, Bradford assays indicated the presence of 1.25 g of protein.

Based upon the original titer in the fermentor, the combined Δ9(Ser)bGH recovered in pure, soluble form in the 18-liter breakthrough fraction and the 8 liter wash from the DE-52 column represents a combined yield on the order of about 30%.

EXAMPLE VI

Purification and Activation of Δ9(Ser)bGH

Inclusion bodies obtained from *E. coli*, IMC No. 1 (ATCC 53030) are extracted in 100 volumes of CB containing 1% SDS by stirring overnight. The resulting extract is refrigerated at 0° C. for 4 hours. Precipitated SDS and residual insoluble inclusion body material are removed by centrifugation. The clarified extract, after coming to room temperature, is chromatographed over a packed AG11A8 column equilibrated with CB at a linear flow rate of 0.3 cm/min. The fractions containing protein are pooled and loaded onto a column of DEAE-Sepharose Fast Flow which has been equilibrated in CB, the pH of which has been adjusted to 9.0 with concentrated HCl. The column is developed with CB containing 0.1 M NaCl. The Δ9(Ser)bGH-containing fractions are pooled, concentrated roughly 5-fold over a PM-10 ultrafiltration membrane, dialyzed into 5 mM Tris-HCl, pH 7.4, and lyophilized to yield the final product.

EXAMPLE VII

Determination of Residual SDS in Purified, Activated Proteins

Each of the final protein solutions obtained in Examples I through IV was analyzed to determine the amount of residual SDS, if any, which was present. The SDS content of the final product was determined by preparing a 10 mg/ml solution in CB. A 100-μl aliquot of this solution was mixed with an equal volume of 1% acridine orange in 0.5 M $NaHSO_4$. Three ml of toluene were added and the tube capped and shaken vigorously for 3 minutes. The aqueous and organic phases were separated by centrifugation for 5 minutes in a clinical centrifuge. The top (toluene) layer was removed to a glass cuvette and its absorbance at 499 nm determined. The SDS level was determined from a standard curve constructed by performing this operation on a series of SDS solutions of known concentration (range 0–150 μg/ml). In each instance, the SDS level was below the quantitative lower limit of the assay (around 10 μg/ml).

What is claimed is:

1. A method for purifying and recovering as biologically active a protein which is produced as an insoluble, biologically inactive inclusion body in a transformant microorganism which comprises:
   (a) extracting the inclusion bodies into a buffered solution of sodium dodecyl sulfate to solubilize the protein;
   (b) chromatographing the protein solution on an ion-retardation resin to remove the sodium dodecyl sulfate from the protein and recover a biologically active protein; and
   (c) chromatographing the biologically active protein solution from step (b) on an anion-exchange resin thereby recovering a purified biologically active protein.

2. A method as claimed in claim 1, which further comprises removing a portion of the sodium dodecyl sulfate from the protein solution prior to chromatographing it on the ion-retardation resin.

3. A method as claimed in claim 2, wherein the SDS is partially removed, prior to ion-retardation chromatography, by dialyzing the protein solution against a SDS-free buffer solution.

4. A method as claimed in claim 3, wherein about 40% to about 70% of the SDS is removed prior to chromatography on the ion-retardation resin.

5. A method as claimed in claim 2, wherein the SDS is removed, prior to ion-retardation chromatography, by cooling the protein solution to temperature between the freezing point of the solution and about 5° C.

6. A method as claimed in claim 5, wherein about 40% to about 70% of the SDS is removed prior to chromatography on the ion-retardation resin.

7. A method as claimed in claim 1, wherein the protein is an animal growth hormone.

8. A method as claimed in claim 7, wherein the animal growth hormone is bovine growth hormone or a fragment or analog thereof.

9. A method as claimed in claim 7, wherein the animal growth hormone is porcine growth hormone or a fragment or analog thereof.

10. A method as claimed in claim 1, wherein the inclusion bodies are extracted into a buffered solution containing from about 0.1% to 5.0% sodium dodecyl sulfate.

11. A method as claimed in claim 1, wherein the inclusion bodies are extracted into a buffered solution containing about 1% sodium dodecyl sulfate.

12. A method as claimed in claim 1, wherein the sodium dodecyl sulfate solution has a pH from about pH 8.5 to pH 11.

13. A method as claimed in claim 1, wherein the ion-retardation resin is AG11A8.

14. A method as claimed in claim 1, wherein the anion-exchange resin is DE-53.

15. A method as claimed in claim 8, wherein the protein is $\Delta$9(Ser)bGH.

16. A method as claimed in claim 9, wherein the protein is $\Delta$7 pGH.

17. A method as claimed in claim 1, wherein said buffered solution is selected from the group consisting of 0.02 M to 0.1 M ethanolamine-HCl, carbonate-bicarbonate, and borate buffer solutions.

18. A method for purifying and recovering as biologically active a protein which is produced as an insoluble, biologically inactive inclusion body in a transformant microorganism which comprises:
(a) extracting the inclusion bodies into a buffered solution of from about 0.1% to about 5.0% sodium dodecyl sulfate to solubilize the protein, said buffer solution selected from the group consisting of 0.02 M to 0.1 M ethanolamine-HCl, carbonate-bicarbonate, and borate buffer solutions, said buffered solutions having a pH from about pH 8.5 to pH 11;
(b) chromatographing the protein solution on an ion-retardation resin to remove the sodium dodecyl sulfate from the protein and recover a biologically active protein; and
(c) chromatographing the biologically active protein solution from step (b) on an anion-exchange resin thereby recovering a purified biologically active protein.

19. A method as claimed in claim 18, wherein the inclusion bodies are extracted into a buffered solution containing about 1% sodium dodecyl sulfate.

20. A method as claimed in claim 18, wherein the SDS is partially removed, prior to ion-retardation chromatography, by dialyzing the protein solution against a SDS-free buffer solution.

* * * * *